*(12)* United States Patent
Staack et al.

(10) Patent No.: US 10,098,687 B2
(45) Date of Patent: Oct. 16, 2018

(54) NANO DISCHARGES IN LIQUIDS

(71) Applicant: DREXEL UNIVERSITY, Philadelphia, PA (US)

(72) Inventors: David Staack, College Station, TX (US); Alexander Fridman, Philadelphia, PA (US); Alexander F. Gutsol, Lafayette, CA (US); Yury Gogotsi, Ivyland, PA (US); Gennady Friedman, Richboro, PA (US)

(73) Assignee: Drexel University, Philadelphia, PA (US)

( * ) Notice: Subject to any disclaimer, the term of this patent is extended or adjusted under 35 U.S.C. 154(b) by 733 days.

(21) Appl. No.: 14/604,918

(22) Filed: Jan. 26, 2015

(65) Prior Publication Data

US 2015/0141986 A1   May 21, 2015

Related U.S. Application Data

(62) Division of application No. 13/055,998, filed as application No. PCT/US2009/054329 on Aug. 19, 2009, now Pat. No. 8,968,286.
(Continued)

(51) Int. Cl.
*A61B 18/04* (2006.01)
*B82Y 15/00* (2011.01)
(Continued)

(52) U.S. Cl.
CPC ............ *A61B 18/042* (2013.01); *B82Y 15/00* (2013.01); *G01N 21/67* (2013.01); *G01N 27/68* (2013.01); *A61B 2018/00125* (2013.01)

(58) Field of Classification Search
CPC ........ A61B 18/042; A61B 2018/00125; B82Y 15/00; G01N 27/68; G01N 21/67
See application file for complete search history.

(56) References Cited

U.S. PATENT DOCUMENTS 5,968,377 A   10/1999   Yuasa et al.
6,135,998 A   10/2000   Palanker
(Continued)

OTHER PUBLICATIONS

PCT Application No. PCT/US2009/054329 : International Search Report and Written Opinion of the International Searching Authority, dated Feb. 23, 2010, 10 pages.
(Continued)

*Primary Examiner* — Lindsey G Wehrheim
(74) *Attorney, Agent, or Firm* — Baker & Hostetler LLP

(57) ABSTRACT

The present invention is direct to a nano-probe corona tool and uses thereof. A nano-probe corona tool is disclosed having a tip with a diameter in the nano-scale, typically around 100 nm. The nano-probe corona tool is constructed of electrically conductive material. On the other end of the tool, a pulsed voltage source outputs a pulsed voltage to generate a pulsed electrical potential at the tip. The pulsed electrical potential at the tip causes a plasma discharge corona to occur. Uses of the corona discharge include, but are not limited to, optical emission spectroscopy, in the enhancement of deposition of coatings and nanoscale welding, e.g., nanotube or nanowires to a contact pad and welding two nanowires together, and in nanoscale surgery. For example, a nano-probe comprising CNTs may be inserted into cell membranes. The resulting corona discharge may be used to destroy tumors within the cell.

9 Claims, 4 Drawing Sheets

Related U.S. Application Data

(60) Provisional application No. 61/090,151, filed on Aug. 19, 2008.

(51) Int. Cl.
   *G01N 21/67* (2006.01)
   *G01N 27/68* (2006.01)
   *A61B 18/00* (2006.01)

(56) References Cited

U.S. PATENT DOCUMENTS

| | | |
|---|---|---|
| 6,635,996 B1 | 10/2003 | Nakajima et al. |
| 2004/0236321 A1* | 11/2004 | Palanker ............ A61B 18/1402 606/41 |
| 2006/0060464 A1 | 3/2006 | Chang |
| 2006/0197018 A1 | 9/2006 | Chen |
| 2008/0140195 A1* | 6/2008 | Su ...................... A61B 5/04001 623/11.11 |
| 2009/0039790 A1 | 2/2009 | Suslov |
| 2010/0006419 A1 | 1/2010 | Gutsol et al. |
| 2010/0089742 A1 | 4/2010 | Suslov |
| 2010/0145253 A1 | 6/2010 | Gutsol et al. |
| 2010/0219136 A1 | 9/2010 | Campbell et al. |
| 2012/0156091 A1 | 6/2012 | Fridman et al. |
| 2012/0253265 A1 | 10/2012 | Fridman et al. |
| 2013/0310731 A1 | 11/2013 | Gutsol et al. |
| 2014/0074090 A1 | 3/2014 | Lam et al. |

OTHER PUBLICATIONS

PCT Application No. PCT/US2009/054329 : International Preliminary Report on Patentability, dated Feb. 22, 2011, 4 pages.

* cited by examiner

NANO DISCHARGES IN LIQUIDS

CROSS REFERENCE TO RELATED APPLICATIONS

This application is a divisional application of U.S. patent application Ser. No. 13/055,998, filed Jun. 22, 2011, which is a National Stage Entry of PCT/US2009/054329, filed Aug. 19, 2009, which claims priority to U.S. Provisional Patent Application Ser. No. 61/090,151 filed Aug. 19, 2008, the disclosures of which are hereby incorporated by reference in their entireties.

TECHNICAL FIELD

The present invention relates to plasma systems, and in particular, to the use of plasma in liquids.

BACKGROUND

The use of plasma in liquids has various applications. For example, one of the more common ways of performing quantitative analysis of solids and liquids is atomic or optical emission spectroscopy (OES), which measures the optical emissions from excited atoms to determine their concentration. In typical diagnostics, the components of the solution are aspirated into a hot plasma and vaporized, or atomized, by the plasma. While in the plasma, the components are electronically excited. Once removed from the plasma, the excited components decay back to a ground or relaxed state by emitting light having wavelengths associated with their particular atomic structure of the components. This produces narrow emission lines in a spectra that can be used to identify the components.

SUMMARY

The present invention is directed to the generation of non-thermal plasma discharge corona in fluids through the use of a nano-probe corona tool having an electrode with a tip with a nano-scale curvature. This provides for the ability, in some configurations, to generate the corona using minimal power and without creating hot plasma that may destroy or damage the fluid. In one example, a nano-probe corona tool of the present subject matter may be used for in situ optical emission spectrometry (OES) of analyte in volumes on the picoliter to femtoliter scale. In some configurations, the analysis may be done in nanoseconds. In some examples, the nano-probe corona tool may be used for environmental monitoring and chemical process monitoring and as well as the monitoring of biological processes.

In one example of the use of the present subject matter in OES, a tip of a tungsten wire is sharpened to a diameter of less than 100 nm. An appropriate voltage is applied, generating a corona discharge at the tip. The material, or fluid, that comes in contact with the corona discharge is energized to an excited state. The corona discharge is thereafter extinguished and the decay of the excited material is measured. In some examples, the voltage was applied using an alternating power supply generating an alternating potential. The potential was applied to the tip through a circuit comprising a capacitor charging circuit in series with one spark gap circuit used to initiate a voltage pulse and one spark gap circuit used to extinguish the voltage pulse. The time duration, magnitude and repetition of the voltage pulse may be adjusted by varying the spark gap lengths, capacitor size, and charging voltage.

Other materials that may be used for a tip include, but are not limited to, carbon fibers, quartz glass pipettes with tips covered by a metallic film, and template grown noncatalytic chemical vapor deposition (CVD) carbon nano tubes (CNT) having diameters of approximately 200 nm.

These and other features of the subject matter are described below.

BRIEF DESCRIPTION OF THE DRAWINGS

The foregoing summary, as well as the following detailed description of the subject matter is better understood when read in conjunction with the appended drawings. For the purposes of illustration, there is shown in the drawings exemplary embodiments; however, these embodiments are not limited to the specific methods and instrumentalities disclosed. In the drawings.

DETAILED DESCRIPTION OF ILLUSTRATIVE EMBODIMENTS

Figure 1:
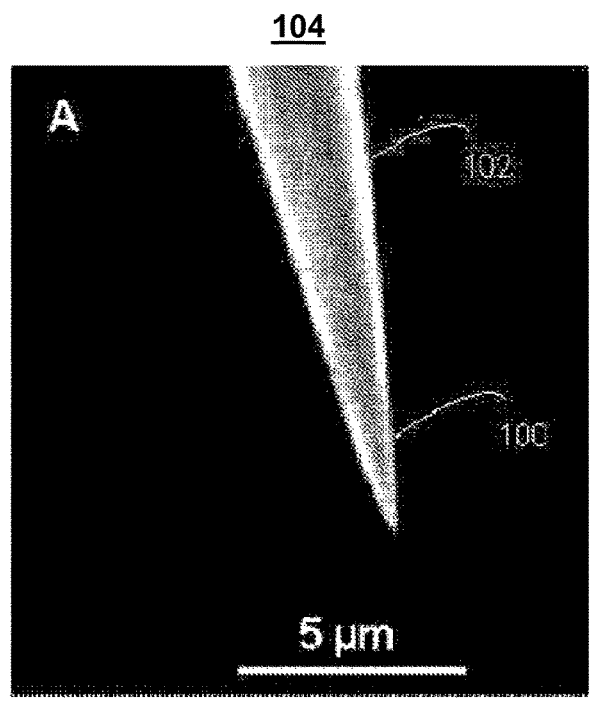
FIG. 1 is an image of the tip of a tungsten wire nano-probe corona tool.

Certain specific details are set forth in the following description and figures to provide a thorough understanding of various embodiments of the subject matter. Certain well-known details often associated with computing and software technology are not set forth in the following disclosure to avoid unnecessarily obscuring the various embodiments of the subject matter. Further, those of ordinary skill in the relevant art will understand that they can practice other embodiments of the subject matter without one or more of the details described below. Finally, while various methods are described with reference to steps and sequences in the following disclosure, the description as such is for providing a clear implementation of embodiments of the subject matter, and the steps and sequences of steps should not be taken as required to practice this subject matter.

The present subject matter involves to the generation of a plasma corona discharge, preferably negative corona, around a nano-probe tip. The plasma corona discharge may be used for various purposes, including, but not limited to, optical emission spectroscopy. When used to analyze a fluid using OES techniques, the nano-probe tip is energized by a pulsed voltage source to cause the generation of a corona discharge. The energy input from the corona discharge into the surrounding fluid energizes a portion of the components in the fluid to an excited state. The components of the fluid that were energized return to a ground or relaxed state. The resulting discharge of various wavelengths of light, or energy, is recorded. A measured wavelength may be used to identify the particular elements or compounds within the material.

It should be understood that although the present subject matter is discussed in terms of its use in OES, the present subject matter may be used in other applications, such as, but not limited to: plasma enhanced chemical deposition from liquid precursors with high productivity and high special resolution; local optical spectroscopy of biological and other fluids; plasma catalysis in the liquid phase for organic fuel conversion or hydrogen sulfide dissociation; and medical device for used in biological procedures such as blood coagulation in a particular capillary.

There are several uses for nanoscale OES probes in microanalysis, analysis of flowing fluids in chemical reactors, including factories on a chip and microfludics chips, in cell biology for measuring calcium concentrations and understanding calcium signaling. The use of narrow band emissions to excite fluorescent proteins locally, without a laser or another external light source, may enable biomolecule detection with 100 nm or better resolution. The present subject matter may be used in forensic research to detect poisons, such as Arsenic, in body fluids or extremely small amounts of food residue. Environmental sensing and monitoring of the vapor condensed from air in a single submicrometer capillary can be done to determine presence of contaminants or toxins. The use of smaller nanotubes or other pointed carbon tips may further decrease the necessary volume to perform an analysis of a fluid.

In addition to diagnostics of a liquid, nanoscale corona discharge can be used for certain plasma chemical processes. For example, a corona discharge generated by a nano-probe of the present subject matter may be used: in the enhancement of deposition of coatings and nanoscale welding, e.g., nanotube or nanowires to a contact pad and welding two nanowires together. In another example, a corona discharge generated by a nano-probe of the present subject matter may be used in nanoscale surgery. For example, a nano-probe comprising CNTs may be inserted into cell membranes. The resulting corona discharge may be used to destroy individual tumor cells. Further, the corona discharge may be used in a precursor of a material such as a metallic film or metallic nanoparticles for deposition onto a surface. The precursor may include, but is not limited to, a metallic salt or metalloorganic compound.

Figure 2:
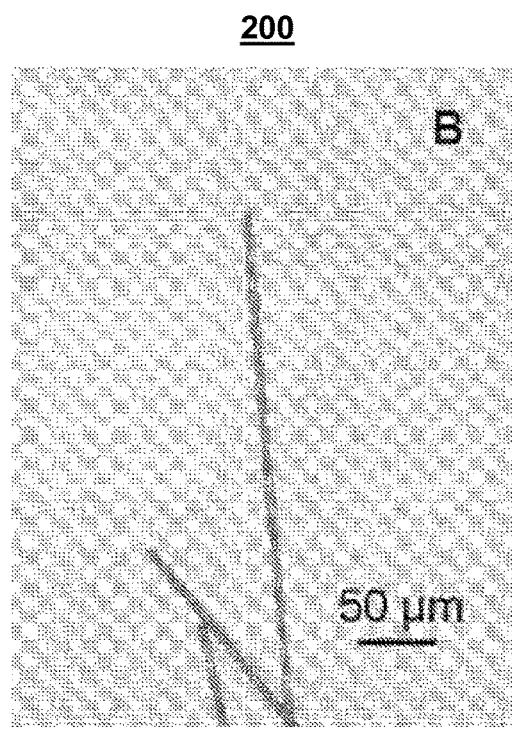
FIG. 2 is an image of the tips of multiple carbon nano tubes configured for use as a nano-probe corona tool.

Various nano-probe tips may be used in conjunction with the present subject matter. Some examples of probes may include, but are not limited to a tungsten wire, a carbon nano tube, a bundle of carbon nano tubes, or a quartz glass pipette partially covered by a metallic film. The metallic film may include several electrically conductive metals or materials, including, but not limited to, gold, silver, platinum, or copper. For example, FIG. 1 shows an image of a tip 100 of a tungsten wire 102 nano-probe corona tool 104 as rendered by a scanning electron microscope. Tip 100 of tungsten wire 102 has been sharpened or shaped, through various methods, to have a cross section, which in FIG. 1 is the diameter, of less than 5 micrometers. A cross sectional measurement of a tip of the present subject matter may vary, but in one example, may range from 1 nm to 10 microns. FIG. 2 is an image of the tips of multiple carbon nano tubes 200 as rendered by a scanning electron microscope. Multiple carbon nanotubes forming a bundle of carbon nano tubes or a single carbon nano tube may be used, depending upon the application or system requirements.

Figure 3:
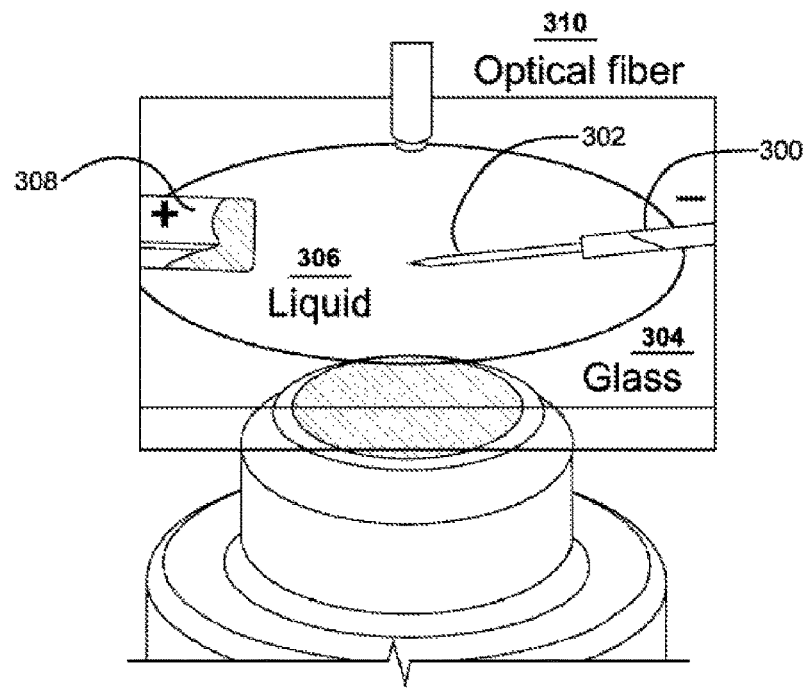
FIG. 3 is an illustration of the use of a tungsten wire nano-probe corona tool for use in optical emission spectroscopy.

FIG. 3 is an illustration of the use of an apparatus for performing optical emission spectroscopy using a tungsten wire. Nano-probe 300, a 10 μm tungsten wire, having tip 302 having a tip with a cross-sectional dimension, diameter in this example, of about 100 nm is placed in liquid 306. Liquid 306 may be found in various locations, such as a product stream of a reactor or a holding tank. Liquid 306 may also be biological in nature, such as tumor or cell.

FIG. 3 illustrates OES analysis of liquid 306 when placed on a substrate, such as glass 304. Pulsed voltage source 308 is in electrical communication with tip 302. Pulsed voltage source 308 generates an electrical field potential that, due to its proximity to tip 302, causes an electrical field to be generated on tip 302. In this example, a negative corona discharge may be achieved with about 3 kV with an estimated breakdown electric field of $1.2 \times 10^{10}$ V/m. The applied voltage may vary, but in one example, the applied voltage is in a range from about 1 V to 12 kV. The plasma discharge corona generated energizes the component of liquid 306 into an excited state. Once the plasma discharge corona is extinguished, optical fiber 310 measures the light emitted from the various components of liquid 306 as the components return to their ground or relaxed state.

Figure 4:
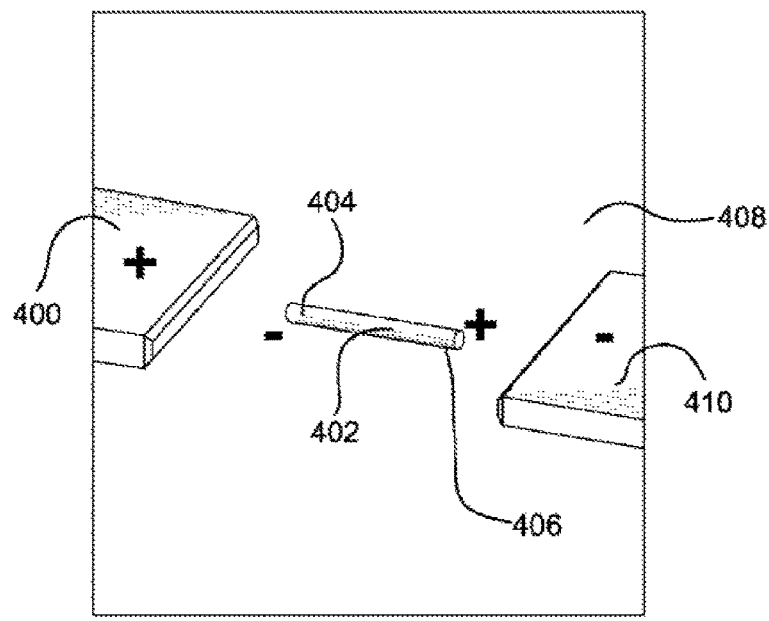
FIG. 4 is an illustration of the use of a carbon nano tube nano-probe corona tool for use in optical emission spectroscopy.

FIG. 4 is an illustration of the an isolated carbon nanotube configured to perform OES on a fluid. Carbon nano tube 402, having tips 404 and 406, is placed in liquid 408. Pulsed voltage source electrode 400 generates electric field pulses that, due to the proximity to tips 404 and 406, causes an electrical field to be generated on tips 404 and 406. The electrical field generated on tips 404 and 406 cause a plasma discharge corona to be developed on tip 404, tip 406 or both, depending upon the placement of carbon nano tube 402 within liquid 408. The plasma discharge corona generated energizes the component of liquid 306 into an excited state. Once the plasma discharge corona is extinguished, an optical measurement device (not shown) may be used to measure the light emitted from the various components of liquid 408 as the components return to their ground or relaxed state. Electrode 410 may be an electrode connected to the pulsed voltage source or may be grounded.

In FIGS. 3 and 4, the corona discharges were remotely generated without physically attaching electrodes to the nano-probes. This may provide for the elimination of the need to wire nanoscale objects, i.e. electrodes, to the nano-probes. It should be understood that the nano-probes may also have the electrodes wired directly to the nano-probes. In addition to the negative corona described above, positive corona discharges may occur around the nanoprobe tips.

Figure 5:
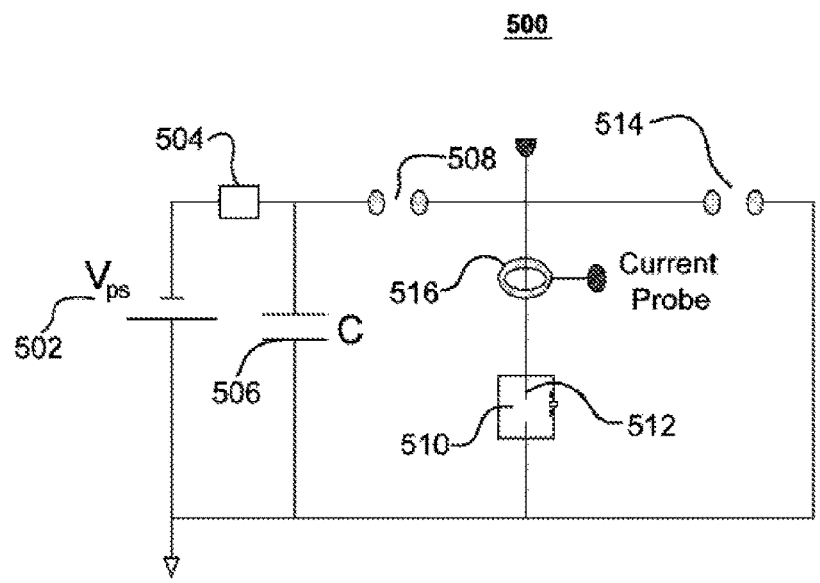
FIG. 5 is an exemplary charging circuit for providing a pulsed voltage source.

Shown in FIG. 5 is a schematic of exemplary electrical circuit 500 used to generate the discharge pulses. Power supply 502, in this example a direct current power supply configured with reversible polarity, is connected to an RC charging circuit with components resistor 504 and capacitor 506. Power supply 502 outputs a voltage that charges capacitor 506. The electric field potential developed in capacitor 506 builds until the potential is sufficient to cause a breakdown across primary spark gap 508. The size of the gap in primary spark gap 508 determines the voltage applied to the load and the repetition rate of the pulses. In one example, the repetition rate was between 1 Hz and 50 Hz. The speed at which the voltage rises may vary, but in one example, the voltage rise may be more than 100 V/ns (Volts per nanosecond). In one further example, the voltage rise may be at least 500 V/ns.

Once breakdown across primary spark gap 508 occurs, the electrical field potential is applied as a voltage to nano-probe tip 512 which is immersed in fluid 510. The electrical field potential causes a plasma discharge corona to develop around tip 512, energizing a portion of the components of fluid 510 into an excited state. To remove the electrical field potential from tip 512, secondary spark gap 514 may be used. The size of the gap in secondary spark gap 514 also varies the duration of the pulse. To measure the application of the voltage, various measurement devices may be used, such as current probe 516.

Figure 6:
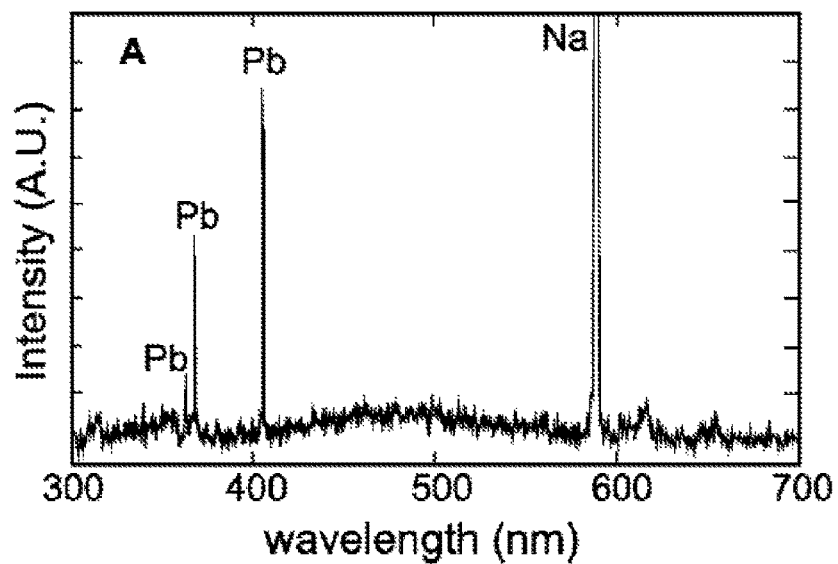
FIG. 6 is an exemplary illustration of the measured wavelength and intensity optical emission spectra resulting from the performance of optical emission spectroscopy utilizing a nano-probe corona tool.
Figure 7:
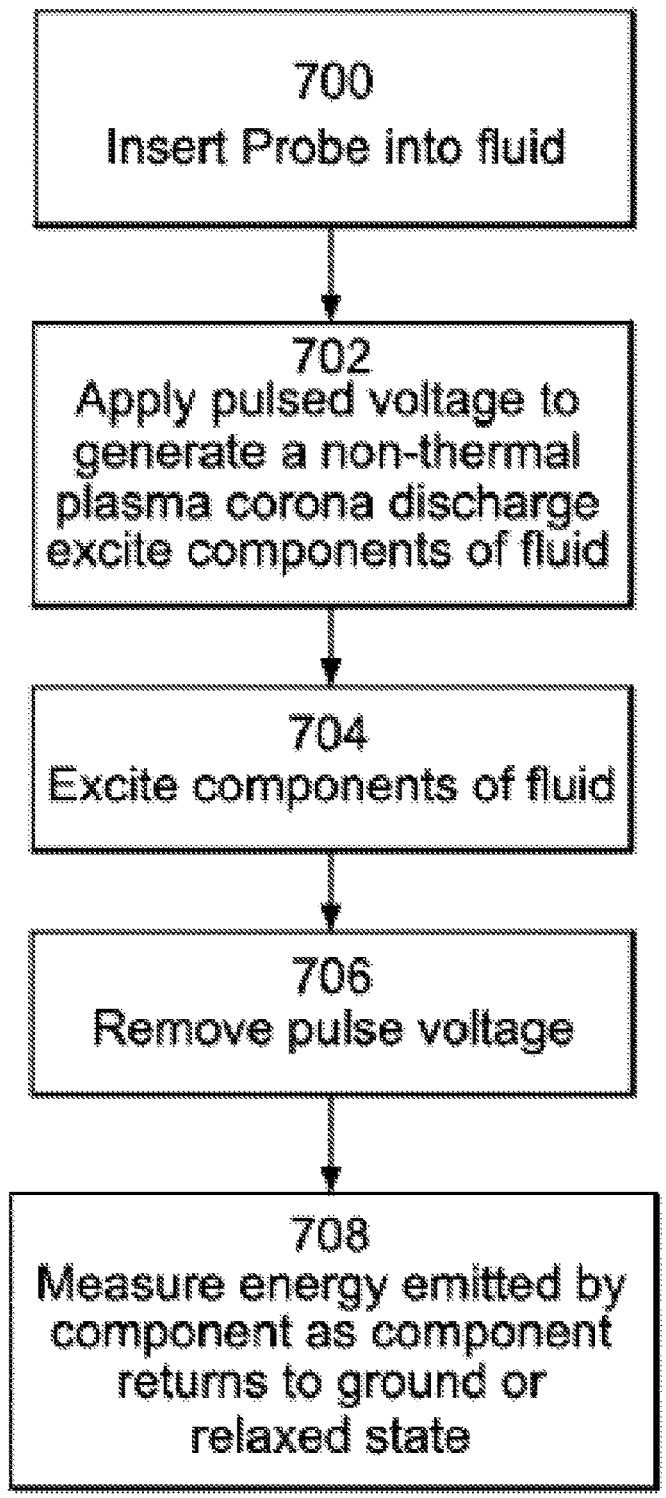
FIG. 7 is an exemplary method of performing optical emission spectroscopy utilizing a nano-probe corona tool.

FIG. 6 is an exemplary illustration of the measured wavelength and intensity optical emission spectra resulting from the performance of optical emission spectroscopy on a fluid containing lead (Pb) and sodium (Na) utilizing a nano-probe corona tool. The emission spectra shown in FIG. 6 may be obtained used an analysis system, such as the one described in FIG. 1, above. The resulting optical emission spectra shows resulting wavelength peaks at approximately 363 nm, 368 nm, and 406 nm. These are common Pb peaks. Thus, through the resulting optical emission spectra, it may be shown that the fluid contained lead.

is an exemplary method for performing optical emission spectra. At least the tip of a nano-probe corona tool is inserted 700 into the fluid undergoing analysis. The fluid may vary, but may include both liquids and gases. A pulsed voltage is applied 702 that causes the generation of a non-thermal plasma corona discharge at the tip of the nano-probe corona tool. The non-thermal plasma corona discharge energizes components of fluid that come in contact with the plasma discharge. This places the components 704 in an excited energy state. The plasma corona discharge is extinguished by removing 706 the pulsed voltage source and the energy emitted by the component is measured as the component relaxes into the reduced energy, or ground, state.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment but rather should be construed in breadth and scope in accordance with the appended claims.

What is claimed:

1. A method of damaging or destroying a tumor, comprising:
   inserting a probe into the tumor, wherein the probe comprises a tip at one end having a diameter of 100 nm;
   applying a pulsed voltage source configured to provide an electrical field pulse to the probe to cause a non-thermal plasma discharge to occur at the tip of the probe;
   applying the pulsed voltage source a predetermined amount of time to damage or destroy the tumor.

2. The method of claim 1, wherein the electrical field pulse has a peak voltage between 1V and 12 kV, a voltage rise greater than 1V/ns, and a duration of from 0.5 ns to 2000 ns.

3. The method of claim 2, wherein the electrical field pulse has a peak voltage between 1V and 4 kV, a voltage rise greater than 1V/ns, and a duration of from 50 ns to 200 ns.

4. The method of claim 2, wherein the voltage rise is greater than 100V/ns.

5. The method of claim 2, wherein the electrical field pulse has a maximum voltage of 3 kV.

6. The method of claim 2, wherein the electrical field pulse has a duration of from 75 nanoseconds to 125 nanoseconds.

7. The method of claim 6, wherein the electrical field pulse has a duration of 100 nanoseconds.

8. The method of claim 1, wherein the probe comprises a tungsten wire, a carbon nano tube, a bundle of carbon nano tubes, or a quartz glass pipette partially covered by a metallic film.

9. The method of claim 8, wherein the metallic film comprises gold, silver, platinum, or copper.

* * * * *